US011618766B2

(12) United States Patent
Shao et al.

(10) Patent No.: US 11,618,766 B2
(45) Date of Patent: Apr. 4, 2023

(54) METHOD FOR PREPARING 16ALPHA-HYDROXYPREDNISOLONE

(71) Applicant: ZHEJIANG SHENZHOU PHARMACEUTICAL COMPANY LIMITED, Zhejiang (CN)

(72) Inventors: Zhenping Shao, Taizhou (CN); Rong Wang, Taizhou (CN); Kegang Chen, Taizhou (CN); Bingqian Wang, Taizhou (CN); Youfu Wang, Taizhou (CN)

(73) Assignee: ZHEJIANG SHENZHOU PHARMACEUTICAL COMPANY LIMITED, Taizhou (CN)

( * ) Notice: Subject to any disclaimer, the term of this patent is extended or adjusted under 35 U.S.C. 154(b) by 0 days.

(21) Appl. No.: 17/933,850

(22) Filed: Sep. 20, 2022

(65) Prior Publication Data

US 2023/0028248 A1 Jan. 26, 2023

Related U.S. Application Data

(63) Continuation of application No. PCT/CN2020/088692, filed on May 6, 2020.

(30) Foreign Application Priority Data

Mar. 20, 2020 (CN) .......................... 202010202320.0

(51) Int. Cl.
 *C07J 7/00* (2006.01)
 *C07B 35/06* (2006.01)
(52) U.S. Cl.
 CPC ............... *C07J 7/006* (2013.01); *C07B 35/06* (2013.01)
(58) Field of Classification Search
 CPC ...................................................... C07J 7/006
 See application file for complete search history.

(56) References Cited

U.S. PATENT DOCUMENTS

| 4,304,727 A | 12/1981 | Heather et al. |
| 5,426,198 A | 6/1995 | Huber |
| 2018/0002372 A1 | 1/2018 | Tripathi et al. |

FOREIGN PATENT DOCUMENTS

| CN | 103724396 A | 4/2014 |
| CN | 105566426 A | 5/2016 |
| CN | 106905406 A | 6/2017 |
| CN | 109384827 A | 2/2019 |
| CN | 109575097 A | 4/2019 |
| CN | 109851653 | 6/2019 |

OTHER PUBLICATIONS

First Office Action in Chinese Application No. 202010202320.0 dated Sep. 24, 2020, 14 pages.
The Second Office Action in Chinese Application No. 202010202320.0 dated Jan. 4, 2021, 13 pages.
Decision to grant a patent in Chinese Application No. 202010202320.0 dated Feb. 9, 2021, 3 pages.
International Search Report in PCT/CN2020/088692 dated Dec. 16, 2020, 7 pages.
Written Opinion in PCT/CN2020/088692 dated Dec. 16, 2020, 8 pages.

*Primary Examiner* — Susanna Moore
(74) *Attorney, Agent, or Firm* — Metis IP LLC

(57) ABSTRACT

Disclosed in the present disclosure is a method for preparing 16alpha-hydroxyprednisolone, belonging to the technical field of medicine preparation and processing. In the method, 21-hydroxypregna-1,4,9(11),16-tetraene-3,20-dione-21-acetate is used as a starting material, and subjected to oxidation, bromo-hydroxylation, debromination and alcoholysis, so as to prepare 16alpha-hydroxyprednisolone. The method for preparing 16alpha-hydroxylprednisolone of the present disclosure can effectively control the generation of impurities in the reaction process by improving the disadvantages of traditional processes, and has a mild reaction process and a high overall conversion rate; and the method of the present disclosure has low requirements for a reaction device and low operation costs, is easy to operate, is suitable for industrial production, and has a good market prospect.

1 Claim, No Drawings

METHOD FOR PREPARING 16ALPHA-HYDROXYPREDNISOLONE

CROSS-REFERENCE TO RELATED APPLICATIONS

This application is a Continuation of International Application No. PCT/CN2020/088692, filed on May 6, 2020, which claims priority of Chinese Patent Application No. 202010202320.0, filed on Mar. 20, 2020, the contents of each of which are hereby incorporated by reference.

TECHNICAL FIELD

The present disclosure relates to the technical field of medicine preparation and processing, and more particularly to a method for preparing 16alpha-hydroxyprednisolone.

BACKGROUND

16alpha-hydroxyprednisolone (a molecular formula of $C_{21}H_{28}O_6$), having a chemical name of 11β,16α,17α,21-tetrahydroxypregna-1,4-diene-3,20-dione, is an important pharmaceutical intermediate for a halogen-free onide-like steroid-adrenocorticoid drug. 16Alpha-hydroxyprednisolone can be used as a raw material to synthesize glucocorticoid drugs such as budesonide, ciclesonide, and desonide. Onide-like glucocorticoid drugs are widely used in the treatment of refractory asthma and inflammations. In particular, budesonide and ciclesonide have the advantages of small dosage, strong local anti-inflammatory effect, small systemic side effects and the like, are more prominently applicable to children, and thus become the first choice for clinical treatment of severe asthma and allergic rhinitis. 16Alpha-hydroxyprednisolone is a basic raw material for the preparation of onide-like glucocorticoid drugs, and has a very broad market prospect.

To find a method for synthesizing 16alpha-hydroxyprednisolone that is safe, easy to operate, low in cost and easy to purify has been focused and researched by chemists for many years.

CN201310698900.3 reported a synthetic route using prednisolone as a starting material, and obtained 16alpha-hydroxyprednisolone through cyclization, ring cleavage, esterification, elimination, oxidation, cyclization, re-hydrolysis and the like.

The method has too many reaction steps, such that more side reaction impurities will be generated when a 16,17-ene compound is prepared by hydroxyl elimination, resulting in low yield. Meanwhile, prednisolone is relatively high in cost and thus not suitable for industrial production.

The reaction route is as follows:

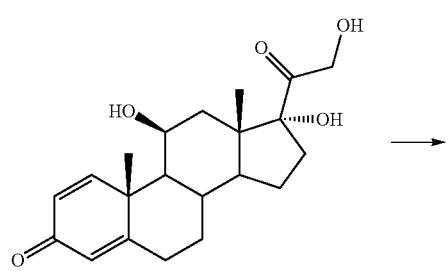

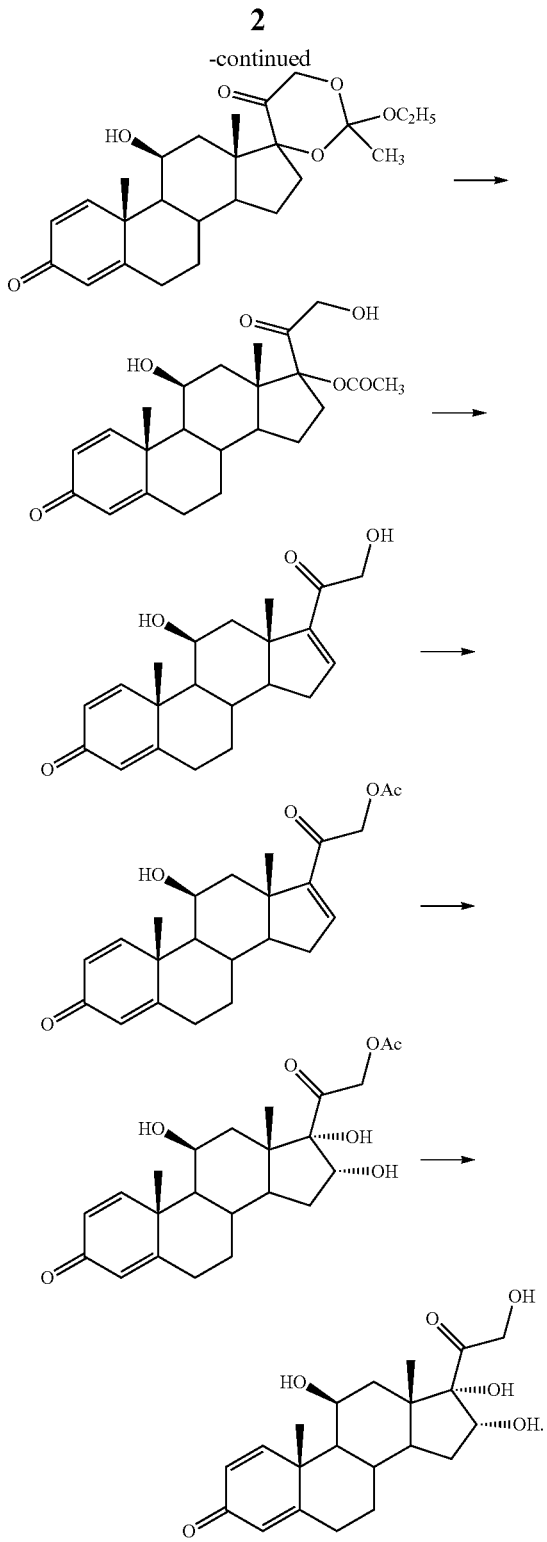

SUMMARY

In order to solve the difficulties in the preparation of 16alpha-hydroxyprednisolone, such as complex process, high cost, difficult removal of impurities, and difficulty in refining, the present disclosure provides a method for preparing 16alpha-hydroxyprednisolone, wherein 21-hydroxypregna-1,4,9(11),16-tetraene-3,20-dione-21-acetate is used as a starting material, and subjected to oxidation, bromohydroxylation, debromination and alcoholysis, so as to prepare the 16alpha-hydroxyprednisolone.

The object of the present disclosure is achieved by the following ways.

A method for preparing 16alpha-hydroxyprednisolone is provided, wherein a synthetic route of the method is as follows:

brominating agent and stirring for reaction; after the completion of the reaction, adding a sodium sulfite solution; removing the organic solvent B by concentration; performing water precipitation, filtering and drying to obtain an intermediate (3);

3) a debromination reaction: dissolving the intermediate (3) in an organic solvent C; adding mercaptoacetic acid, and cooling to −5° C. to 15° C. while stirring; adding a hydro-

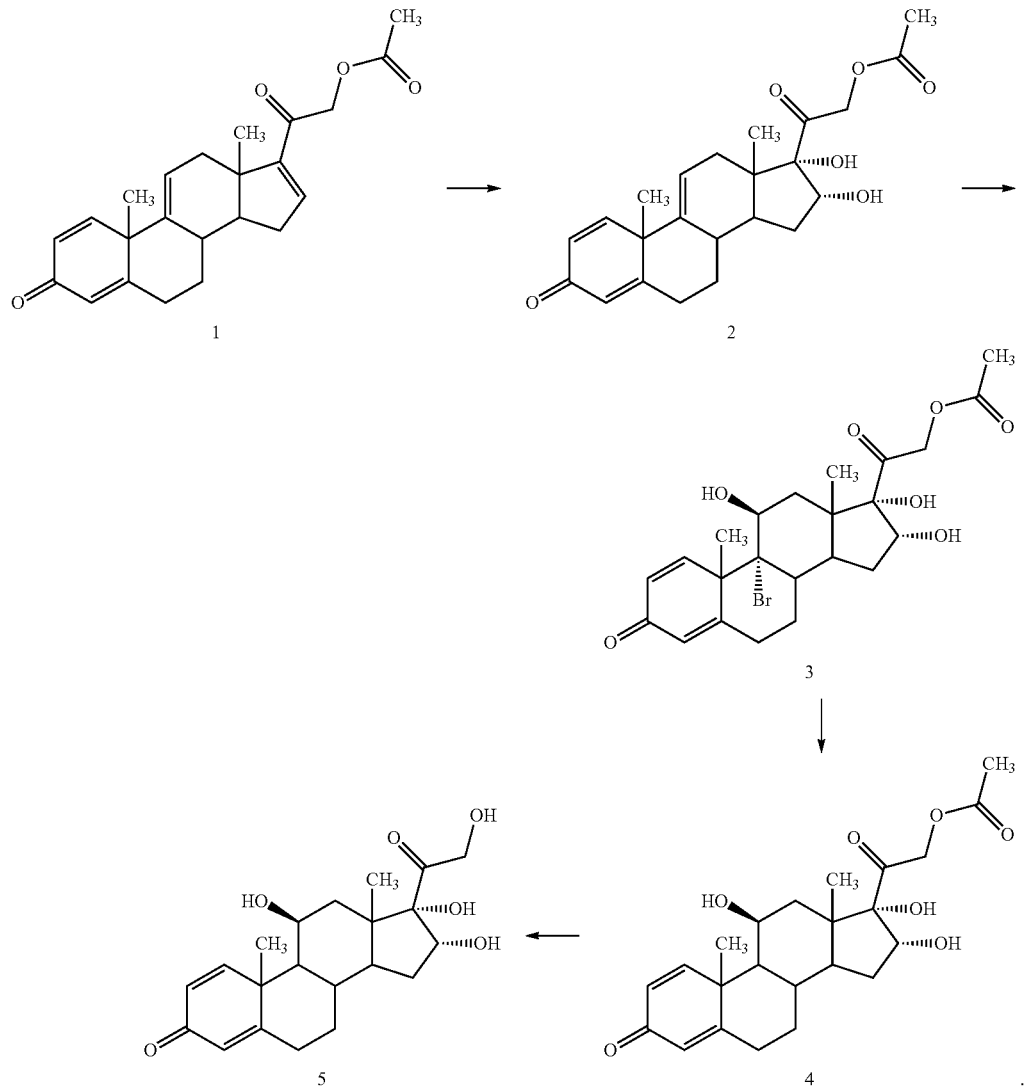

The method specifically comprises the following steps:

1) an oxidation reaction: dissolving 21-hydroxypregna-1,4,9(11),16-tetraene-3,20-dione-21-acetate (1) in an organic solvent A; adding an acid catalyst A, and cooling to −20° C. to −5° C. while stirring; adding a potassium permanganate aqueous solution and stirring for reaction; after the completion of the reaction, adding a sodium bisulfite aqueous solution; collecting a filtrate after filtration, and removing the organic solvent A by concentration; performing water precipitation, filtering and drying to obtain an intermediate (2);

2) a bromo-hydroxylation reaction: dissolving the intermediate (2) in an organic solvent B; adding an acid catalyst B, and cooling to −10° C. to 5° C. while stirring; adding a chloric acid solution of $CrCl_2$ and stirring for reaction; after the completion of the reaction, performing water precipitation, filtering and drying to obtain an intermediate (4); and 4) an alcoholysis reaction: dissolving the intermediate (4) in an organic solvent D; cooling to −10° C. to 10° C. while stirring; adding alkali liquor and stirring for reaction; after the completion of the reaction, neutralizing with acetic acid, and removing the organic solvent D by concentration; performing water precipitation, filtering and drying to obtain a crude product; refining the crude product once with the organic solvent D to obtain the 16alpha-hydroxyprednisolone (5).

Further, the organic solvent A in the step 1) is one of acetone, butanone and dichloromethane, and has a usage amount in volume of 30 to 50 times of the weight of the substrate 21-hydroxypregna-1,4,9(11),16-tetraene-3,20-dione-21-acetate (1); the acid catalyst A is formic acid, oxalic acid or glacial acetic acid, and has a usage amount of 1.5 to 2.5 times of the molar amount of the substrate 21-hydroxypregna-1,4,9(11),16-tetraene-3,20-dione-21-acetate (1); the potassium permanganate aqueous solution has a mass concentration of 6% to 10%, and a usage amount of 1.1 to 1.5 times of the molar amount of the substrate 21-hydroxypregna-1,4,9(11),16-tetraene-3,20-dione-21-acetate (1); and the sodium bisulfite aqueous solution has a mass concentration of 5% to 20%, and a usage amount of 1.5 to 2.5 times of the molar amount of the substrate 21-hydroxypregna-1,4,9(11),16-tetraene-3,20-dione-21-acetate (1).

Further, the organic solvent B in the step 2) is one of acetone and butanone, and has a usage amount in volume of 20 to 40 times of the weight of the intermediate (2); the acid catalyst B is one of perchloric acid, fluoroboric acid, trifluoroacetic acid and methanesulfonic acid, and has a mass concentration of 2% to 10%, and a usage amount of 0.3 to 0.5 times of the molar amount of the intermediate (2); the brominating agent is one of N-bromosuccinimide and dibromohydantoin, and has a usage amount of 1.8 to 2.5 times of the molar amount of the intermediate (2); and the sodium sulfite aqueous solution has a mass concentration of 5% to 20%, and a usage amount of 0.5 to 1.0 times of the molar amount of the intermediate (2).

Further, the organic solvent C in the step 3) is one of N,N-dimethylformamide and tetrahydrofuran, and has a usage amount in volume of 5 to 10 times of the weight of the intermediate (3); the mercaptoacetic acid has a usage amount of 4 to 10 times of the molar amount of the intermediate (3); and the hydrochloric acid solution of $CrCl_2$ has a mass concentration of 30% to 50%, and a usage amount of 3 to 10 times of the molar amount of the intermediate (3).

Further, the organic solvent D in the step 4) is a mixture of dichloromethane and methanol/ethanol/propanol in a volume ratio of 1:1 to 3:1, and has a usage amount in volume of 15 to 30 times of the weight of the intermediate (4); the alkali liquor is one of a methanol solution of sodium hydroxide, a methanol solution of potassium hydroxide and a methanol solution of potassium carbonate, and has a mass concentration of 2% to 10%, and a usage amount of 0.4 to 0.9 times of the molar amount of the intermediate (4); and the acetic acid has a mass concentration of 5% to 50%, and a usage amount of 0.4 to 0.9 times of the molar amount of the intermediate (4).

All the raw materials involved in the method of the present disclosure can be fully obtained by commercially available methods.

Compared with the prior art, the present disclosure has the following technical effects.

1. In the oxidation reaction step of the present disclosure, potassium permanganate has a relatively high oxidizing property, and thus has higher requirements on equipment and also easily produces impurities in the reaction process. Therefore, in the present disclosure, the reaction temperature is controlled at −20° C. to −5° C. during the oxidation process, and the mass concentration of the potassium permanganate aqueous solution is controlled at 6% to 10%, which can effectively avoid the above problems and improve the reaction efficiency.

2. In the debromination reaction step of the present disclosure, the mercaptoacetic acid and the hydrochloric acid solution of $CrCl_2$ are used, which have higher reactivity and can shorten the reaction time. Traditionally, a combination of mercaptoacetic acid, zinc powder and $CrCl_3$ is used for a debromination reaction. Due to the heavy weight, zinc powder is not easy to stir evenly, but easy to agglomerate during the reaction, resulting in incomplete reaction and being not suitable for mass production.

3. Since no zinc powder is used in the key debromination step of the present disclosure, the reaction temperature can be significantly reduced and needs to be controlled at −5° C. to 15° C., so that the generation of impurities can be effectively controlled, the reaction yield is increased, and the cost can also be reduced by 15%-20%.

4. The reaction of the present disclosure is mild, the overall conversion rate is higher than 70%, and the purity is higher than 99.5%.

5. The method of the present disclosure has low requirements for a reaction device, is low in operating cost, simple to operate and suitable for industrial production, and has a good market prospect.

DETAILED DESCRIPTION

The present disclosure will be further described below with reference to the embodiments, which are not intended to limit the present disclosure.

The specific experimental steps or conditions which are not described in the embodiments can be carried out according to the operations of the conventional experimental methods described in the publications in this field. The reagents or equipment used without the manufacturer's indications are conventional products that can be obtained from the market.

Example 1: Preparation of 16alpha-hydroxyprednisolone 1) an oxidation reaction: dissolving 50 g of 21-hydroxypregna-1,4,9(11),16-tetraene-3,20-dione-21-acetate (1) in 2000 mL of acetone; adding 10 mL of formic acid, and cooling to −10° C. while stirring; adding 300 mL of 8% potassium permanganate aqueous solution and stirring for reaction; after the completion of the reaction, adding 200 mL of 10% sodium bisulfite aqueous solution; collecting a filtrate after filtration, and removing the acetone by concentration; performing water precipitation, filtering and drying to obtain 50 g of intermediate (2);

2) a bromo-hydroxylation reaction: dissolving 50 g of the intermediate (2) in 2000 mL of butanone; adding 120 mL of fluoboric acid having a mass concentration of 2%, and cooling to 5° C. while stirring; adding 50 g of dibromohydantoin and stirring for reaction; after the completion of the reaction, adding 70 mL of 15% sodium sulfite aqueous solution; removing the butanone by concentration; performing water precipitation, filtering and drying to obtain 60 g of intermediate (3);

3) a debromination reaction: dissolving 60 g of the intermediate (3) in 300 mL of N,N-dimethylformamide; adding 60 mL of mercaptoacetic acid, and cooling to 5° C. while stirring; adding 250 mL of 30% hydrochloric acid solution of $CrCl_2$ and stirring for reaction; after the completion of the reaction, performing water precipitation, filtering and drying to obtain 45 g of intermediate (4); and 4) an alcoholysis reaction: dissolving 45 g of the intermediate (4) in a mixed organic solvent of 500 mL of dichloromethane and 500 mL of methanol; cooling to 0° C. while stirring; adding 90 mL of 2% methanol solution of sodium hydroxide and stirring for reaction; after the completion of the reaction, neutralizing with acetic acid having a mass concentration of 5%, and removing the mixed organic solvent by concentration; performing water precipitation, filtering and drying to obtain 38 g of crude product of 16alpha-hydroxyprednisolone; refining the crude product once with the above mixed solvent to obtain 35.5 g of 16alpha-hydroxyprednisolone, wherein the product has a melting point of 236.1-237.2° C., 99.8% HPLC, and total mass yield of 71%.

Example 2: Preparation of 16alpha-hydroxyprednisolone 1) an oxidation reaction: dissolving 50 g of 21-hydroxy-pregna-1,4,9(11),16-tetraene-3,20-dione-21-acetate (1) in 1500 mL of butanone; adding 20 mL of oxalic acid, and cooling to −5° C. while stirring; adding 350 mL of 6% potassium permanganate aqueous solution and stirring for reaction; after the completion of the reaction, adding 400 mL of 5% sodium bisulfite aqueous solution; collecting a filtrate after filtration, and removing the butanone by concentration; performing water precipitation, filtering and drying to obtain 50.5 g of intermediate (2);

2) a bromo-hydroxylation reaction: dissolving 50.5 g of the intermediate (2) in 1500 mL of acetone; adding 70 mL of perchloric acid having a mass concentration of 5%, and cooling to 0° C. while stirring; adding 45 g of N-bromo-succinimide and stirring for reaction; after the completion of the reaction, adding 50 mL of 20% sodium sulfite aqueous solution; removing the acetone by concentration; performing water precipitation, filtering and drying to obtain 62 g of intermediate (3);

3) a debromination reaction: dissolving 62 g of the intermediate (3) in 400 mL of tetrahydrofuran; adding 50 mL of mercaptoacetic acid, and cooling to −5° C. while stirring; adding 200 mL of 40% hydrochloric acid solution of CrCl$_2$ and stirring for reaction; after the completion of the reaction, performing water precipitation, filtering and drying to obtain 46 g of intermediate (4); and 4) an alcoholysis reaction: dissolving 46 g of the intermediate (4) in a mixed solvent of 700 mL of dichloromethane and 400 mL of ethanol; cooling to −10° C. while stirring; adding 50 mL of 8% methanol solution of potassium hydroxide and stirring for reaction; after the completion of the reaction, neutralizing with acetic acid having a mass concentration of 25%, and removing the organic solvent by concentration; performing water precipitation, filtering and drying to obtain 39 g of crude product of 16alpha-hydroxy-prednisolone; refining the crude product once with the above mixed solvent to obtain 36 g of 16alpha-hydroxypredniso-lone, wherein the product has a melting point of 236.3-237.4° C., 99.7% HPLC, and total mass yield of 72%.

Example 3: Preparation of 16alpha-hydroxyprednisolone 1) an oxidation reaction: dissolving 50 g of 21-hydroxy-pregna-1,4,9(11),16-tetraene-3,20-dione-21-acetate (1) in 1500 mL of dichloromethane; adding 15 mL of glacial acetic acid, and cooling to −20° C. while stirring; adding 320 mL of 7% potassium permanganate aqueous solution and stirring for reaction; after the completion of the reaction, adding 100 mL of 20% sodium bisulfite aqueous solution; collecting a filtrate after filtration, and removing the organic solvent by concentration; performing water precipitation, filtering and drying to obtain 50.1 g of intermediate (2);

2) a bromo-hydroxylation reaction: dissolving 50.1 g of the intermediate (2) in 2000 g of acetone; adding 50 mL of methanesulfonic acid having a mass concentration of 10%, and cooling to −10° C. while stirring; adding 48 g of N-bromosuccinimide and stirring for reaction; after the completion of the reaction, adding 80 mL of 5% sodium sulfite aqueous solution; removing the organic solvent by concentration; performing water precipitation, filtering and drying to obtain 61 g of intermediate (3);

3) a debromination reaction: dissolving 61 g of the intermediate (3) in 350 mL of tetrahydrofuran; adding 55 mL of mercaptoacetic acid, and cooling to 15° C. while stirring; adding 70 mL of 50% hydrochloric acid solution of CrCl$_2$ and stirring for reaction; after the completion of the reaction, performing water precipitation, filtering and drying to obtain 45.5 g of intermediate (4); and 4) an alcoholysis reaction: dissolving 45.5 g of the intermediate (4) in a mixed organic solvent of 900 mL of dichloromethane and 300 mL of propanol; cooling to 10° C. while stirring; adding 70 mL of 10% methanol solution of potassium carbonate and stirring for reaction; after the completion of the reaction, neutralizing with acetic acid having a mass concentration of 50%, and removing the mixed organic solvent by concentration; performing water precipitation, filtering and drying to obtain 38 g of crude product of 16alpha-hydroxyprednisolone; refining the crude product once with the above mixed organic solvent to obtain 35.7 g of 16alpha-hydroxyprednisolone, wherein the product has a melting point of 236.1-237.3° C., 99.8% HPLC, and total mass yield of 71.4%.

The above is only the detailed description of the present disclosure, but the protection scope of the present disclosure is not limited thereto. Within the technical scope disclosed in the present disclosure, any equivalent modifications or replacements easily derived by a person skilled in the art shall fall within the protection scope of the present disclosure.

What is claimed is:
1. A method for preparing 16alpha-hydroxyprednisolone, wherein a synthetic route of the method is as follows:

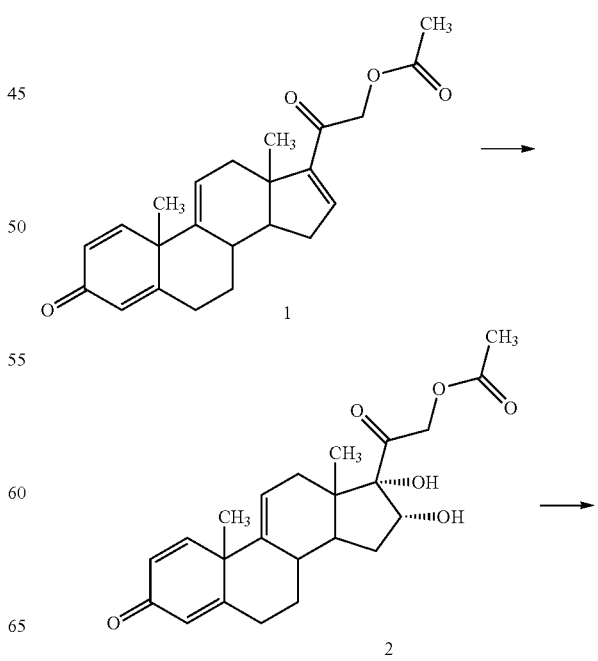

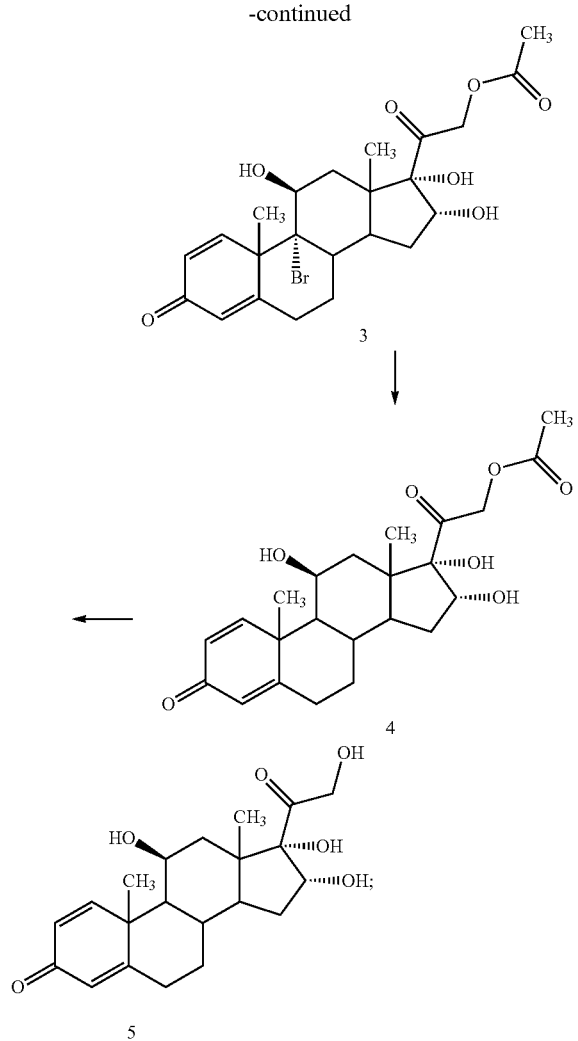

the method comprises the following steps:

1) an oxidation reaction: dissolving a compound (1) in an organic solvent A; adding an acid catalyst A, and cooling to −20° C. to −5° C. while stirring; adding a potassium permanganate aqueous solution and stirring for reaction; after the completion of the reaction, adding a sodium bisulfite aqueous solution; collecting a filtrate after filtration, and removing the organic solvent A by concentration; performing water precipitation, filtering and drying to obtain an intermediate (2), wherein the organic solvent A is one of acetone, butanone, and dichloromethane, and has a usage amount in volume of 30 to 50 times of the weight of the compound (1); the acid catalyst A is formic acid, oxalic acid, or glacial acetic acid, and has a usage amount of 1.5 to 2.5 times of the molar amount of the compound (1); the potassium permanganate aqueous solution has a mass concentration of 6% to 10%, and a usage amount of 1.1 to 1.5 times of the molar amount of the compound (1); and the sodium bisulfite aqueous solution has a mass concentration of 5% to 20%, and a usage amount of 1.5 to 2.5 times of the molar amount of the compound (1);

2) a bromo-hydroxylation reaction: dissolving the intermediate (2) in an organic solvent B; adding an acid catalyst B, and cooling to −10° C. to 5° C. while stirring; adding a brominating agent and stirring for reaction; after the completion of the reaction, adding a sodium sulfite solution; removing the organic solvent B by concentration; performing water precipitation, filtering and drying to obtain an intermediate (3), wherein the organic solvent B is one of acetone and butanone, and has a usage amount in volume of 20 to 40 times of the weight of the intermediate (2); the acid catalyst B is one of perchloric acid, fluoroboric acid, trifluoroacetic acid, and methanesulfonic acid, and has a mass concentration of 2% to 10%, and a usage amount of 0.3 to 0.5 times of the molar amount of the intermediate (2); the brominatinq agent is one of N-bromosuccinimide and dibromohydantoin, and has a usage amount of 1.8 to 2.5 times of the molar amount of the intermediate (2); and the sodium sulfite aqueous solution has a mass concentration of 5% to 20%, and a usage amount of 0.5 to 1.0 times of the molar amount of the intermediate (2);

3) a debromination reaction: dissolving the intermediate (3) in an organic solvent C; adding mercaptoacetic acid, and cooling to −5° C. to 15° C. while stirring; adding a hydrochloric acid solution of CrCl2 and stirring for reaction; after the completion of the reaction, performing water precipitation, filtering and drying to obtain an intermediate (4), wherein the organic solvent C is one of N,N-dimethylformamide and tetrahydrofuran, and has a usage amount in volume of 5 to 10 times of the weight of the intermediate (3); the mercaptoacetic acid has a usage amount of 4 to 10 times of the molar amount of the intermediate (3); and the hydrochloric acid solution of CrCl2 has a mass concentration of 30% to 50%, and a usage amount of 3 to 10 times of the molar amount of the intermediate (3); and 4) an alcoholysis reaction: dissolving the intermediate (4) in an organic solvent D; cooling to −10° C. to 10° C. while stirring; adding alkali liquor and stirring for reaction; after the completion of the reaction, neutralizing with acetic acid, and removing the organic solvent D by concentration; performing water precipitation, filtering; and drying to obtain a crude product; refining the crude product once with the organic solvent D to obtain the 16alpha-hydroxyprednisolone (5), wherein the organic solvent D is a mixture of dichloromethane and methanol/ethanol/propanol in a volume ratio of 1:1 to 3:1, and has a usage amount in volume of 15 to 30 times of the weight of the intermediate (4); the alkali liquor is one of a methanol solution of sodium hydroxide, a methanol solution of potassium hydroxide and a methanol solution of potassium carbonate, and has a mass concentration of 2% to 10%, and a usage amount of 0.4 to 0.9 times of the molar amount of the intermediate (4); and the acetic acid has a mass concentration of 5% to 50%, and a usage amount of 0.4 to 0.9 times of the molar amount of the intermediate (4).

* * * * *